(12) United States Patent
Lin et al.

(10) Patent No.: US 7,471,976 B2
(45) Date of Patent: Dec. 30, 2008

(54) DEVICE FOR MEASURING ELECTROCARDIOGRAM WITH TAPELESS FORMAT AND ITS METHOD

(75) Inventors: Kang-Ping Lin, 3F., No. 12, Lane 76, Sec. 2, Jhongbei Rd., Jhongli City, Taoyuan County (TW); Chih-Hui Hsieh, Jhudong Township, Hsinchu County (TW)

(73) Assignee: Kang-Ping Lin, Taoyuan County (TW)

( * ) Notice: Subject to any disclaimer, the term of this patent is extended or adjusted under 35 U.S.C. 154(b) by 202 days.

(21) Appl. No.: 10/753,388

(22) Filed: Jan. 9, 2004

(65) Prior Publication Data
US 2005/0154324 A1 Jul. 14, 2005

(30) Foreign Application Priority Data
Aug. 20, 2003 (TW) ............................... 92122942 A

(51) Int. Cl.
*A61B 5/0404* (2006.01)
(52) U.S. Cl. ....................................... 600/509; 600/523
(58) Field of Classification Search ................ 600/503, 600/509, 523, 515, 382, 384, 520, 521
See application file for complete search history.

(56) References Cited

U.S. PATENT DOCUMENTS

| | | | | | |
|---|---|---|---|---|---|
| 3,724,455 | A | * | 4/1973 | Unger | 600/515 |
| 4,129,125 | A | * | 12/1978 | Lester et al. | 600/484 |
| 4,606,352 | A | * | 8/1986 | Geddes et al. | 600/515 |
| 4,844,090 | A | * | 7/1989 | Sekine | 600/509 |
| 4,865,039 | A | * | 9/1989 | Dunseath, Jr. | 600/410 |
| 5,191,891 | A | * | 3/1993 | Righter | 600/523 |
| 5,289,824 | A | * | 3/1994 | Mills et al. | 600/508 |
| 5,317,269 | A | * | 5/1994 | Mills et al. | 324/427 |
| 5,464,021 | A | * | 11/1995 | Birnbaum | 600/509 |
| 5,613,495 | A | * | 3/1997 | Mills et al. | 600/509 |
| 5,713,365 | A | * | 2/1998 | Castelli | 600/509 |
| 5,738,104 | A | * | 4/1998 | Lo et al. | 600/521 |
| 5,928,141 | A | | 7/1999 | Castelli | |
| 6,241,684 | B1 | * | 6/2001 | Amano et al. | 600/531 |
| 6,345,196 | B1 | | 2/2002 | Castelli | |
| 6,363,274 | B1 | * | 3/2002 | Scalisi et al. | 600/523 |
| 6,714,814 | B2 | * | 3/2004 | Yamada et al. | 600/547 |
| 6,790,178 | B1 | * | 9/2004 | Mault et al. | 600/300 |
| 2002/0095093 | A1 | * | 7/2002 | Au et al. | 600/509 |
| 2003/0120164 | A1 | * | 6/2003 | Nielsen et al. | 600/513 |
| 2005/0148889 | A1 | * | 7/2005 | Chen | 600/509 |

FOREIGN PATENT DOCUMENTS

TW      503735      9/2002

* cited by examiner

*Primary Examiner*—George R Evanisko
*Assistant Examiner*—Michael Kahelin
(74) *Attorney, Agent, or Firm*—Rosenberg, Klein & Lee

(57) ABSTRACT

A device for measuring an electrocardiogram with a tapeless format and its method is provided with electrodes having a flat shape that are contacted by root portions between two fingers of a user's hands or by two fingers of each of the user's hands. The electrocardiogram can be measured directly by that contact, without adding any conductive liquid or gel material.

5 Claims, 10 Drawing Sheets

DEVICE FOR MEASURING ELECTROCARDIOGRAM WITH TAPELESS FORMAT AND ITS METHOD

FIELD OF THE INVENTION

The present invention is directed to a device for measuring an electrocardiogram with tapeless format and its method. In particular, the present invention is directed to an electrocardiogram measuring device which measures electrocardiogram signals via electrodes with a flat shape for being respectively contacted with portions of a user's hands disposed between two fingers of each hand or electrodes embedded thereon for being contacted with two fingers of each of a user's two hands. The invention can display the electrocardiogram measured directly without adding any electric conductive material.

BACKGROUND OF THE INVENTION

With more and more conveniences being in our daily lives, human beings lack the exercise that they should have. As a result, human beings are subject to all kinds of modern diseases. Due to this situation, fitness clubs or gymnasia have rapidly been established to provide exercise space for people living in the city to improve their health. Also, personal medical instruments have been produced, wherein the instruments to detect the heart's blood vessels are the greatest in number.

Traditionally, two wrists, two ankles and some surfaces of a patient's body must be pasted with a layer of conductive material or electrode pieces while having electrocardiography in a hospital. If the patient's symptoms include a fever, the patient would be uncomfortable while taking off their shirt and pants, having a sticky conductive material smeared on their body, and furthermore, having some electrode pieces clamping and adhering to two wrists, two ankles and their chest. Hence, Taiwan Patent Number 503735 shows the latest product, referring to FIG. 1, which is prior art with respect to the present invention. The prior art comprises a shell 1A with a display 2A, two electrode touching keys 5A, plural function keys 6A, a pipe line 3A connected to a wrist air bag 4A. As understood from FIG. 1, the wrist air bag 4A wraps around a wrist and then the two electrode touching keys 5A are filled out with conductive liquid, continuously two finger tips touch the two electrode touching keys 5A for sensing relative electric signals about a heart's blood vessels so as to present results on the display 2A after calculations have been done. However, this prior art still needs to add conductive liquid to the electrode touching keys 5A when collecting relevant information. Additionally, a can loaded with conductive liquid occupies storage space, and would be inconvenient to carry. On the other hand, the method of adding the conductive liquid may be improved or avoided.

SUMMARY OF THE INVENTION

The present invention is a device for measuring an electrocardiogram with a tapeless format and its method, to solve the inconvenience and uncomfortable feeling caused by the method of adhering electrode pieces and pasting conductive liquid. The present invention only needs two metal electrodes with thin shapes clampingly engaged by portions of a user's hands disposed between two fingers of each of a user's right and left hands or electrodes embedded thereon being contacted by two fingers of each of the user's two hands without pasting any conductive liquid thereon to obtain correlative information of the electrocardiogram.

The present invention comprises a shell, shaped as a thin and long cube and having at least one operating panel, the operating panel further comprising at least one button for setting and transferring functions; at least two gelless electrodes with a thin foil shape, slightly embedded and fixed in the operating panel and extending to pass over at least one edge of the shell to a surface on an opposing side of the shell, opposite the operating panel; at least one information display, located on the operating panel to display a plurality of measured values; a calculation system, connected to two gelless electrodes and the information display located in the shell in order to calculate electrical information measured from the gelless electrodes and display the results on the information display. It is to be understood that both the foregoing general description and the following detailed description are exemplary and explanatory only and are not restrictive of the invention, as claimed.

The accompanying drawings, which are incorporated herein and constitute a part of this specification, illustrate several embodiments of the invention and together with the description, serve to explain the principles of the invention.

DESCRIPTION OF THE EMBODIMENTS

Figure 1:
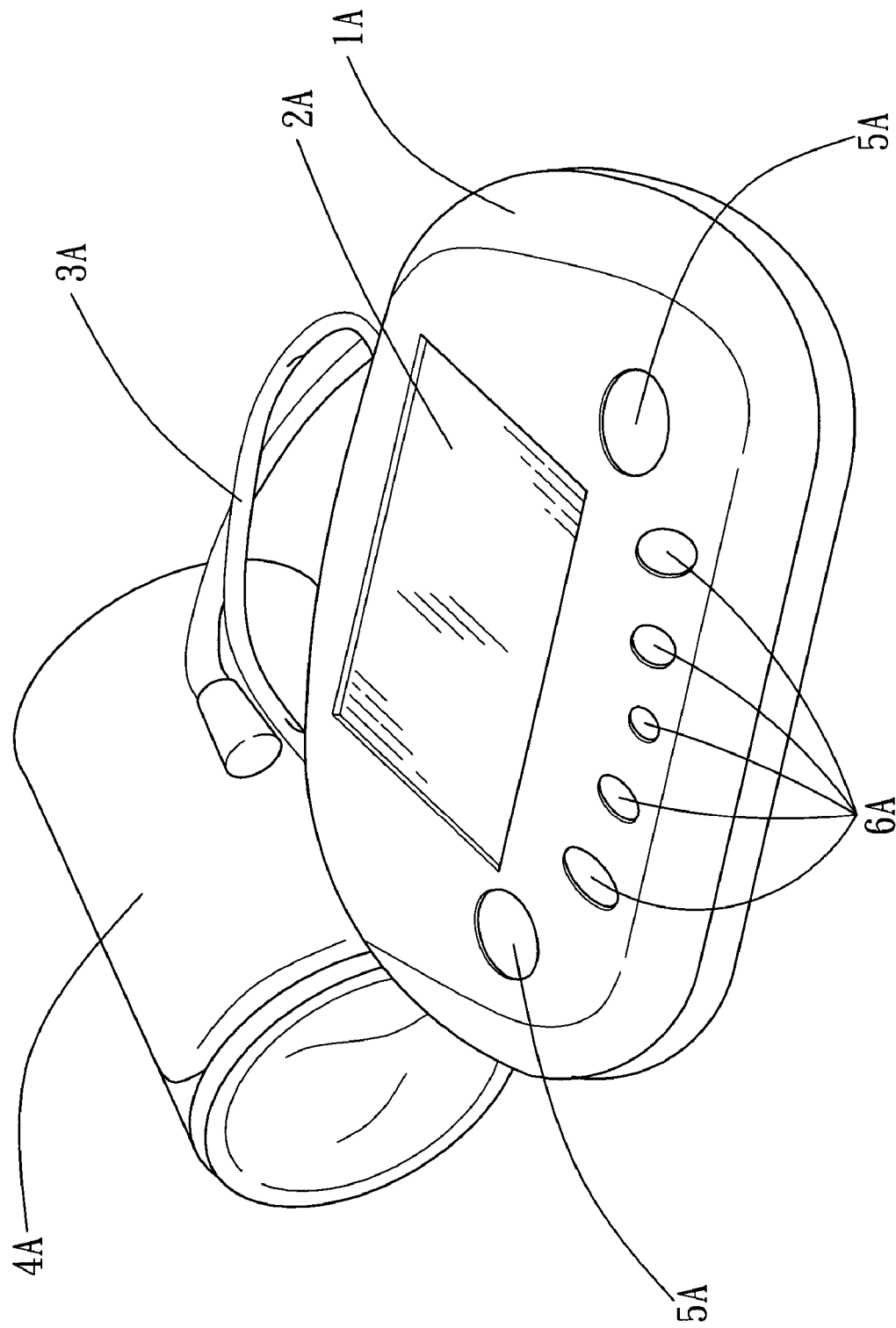
FIG. 1, is a perspective view of a prior art device.
Figure 2:
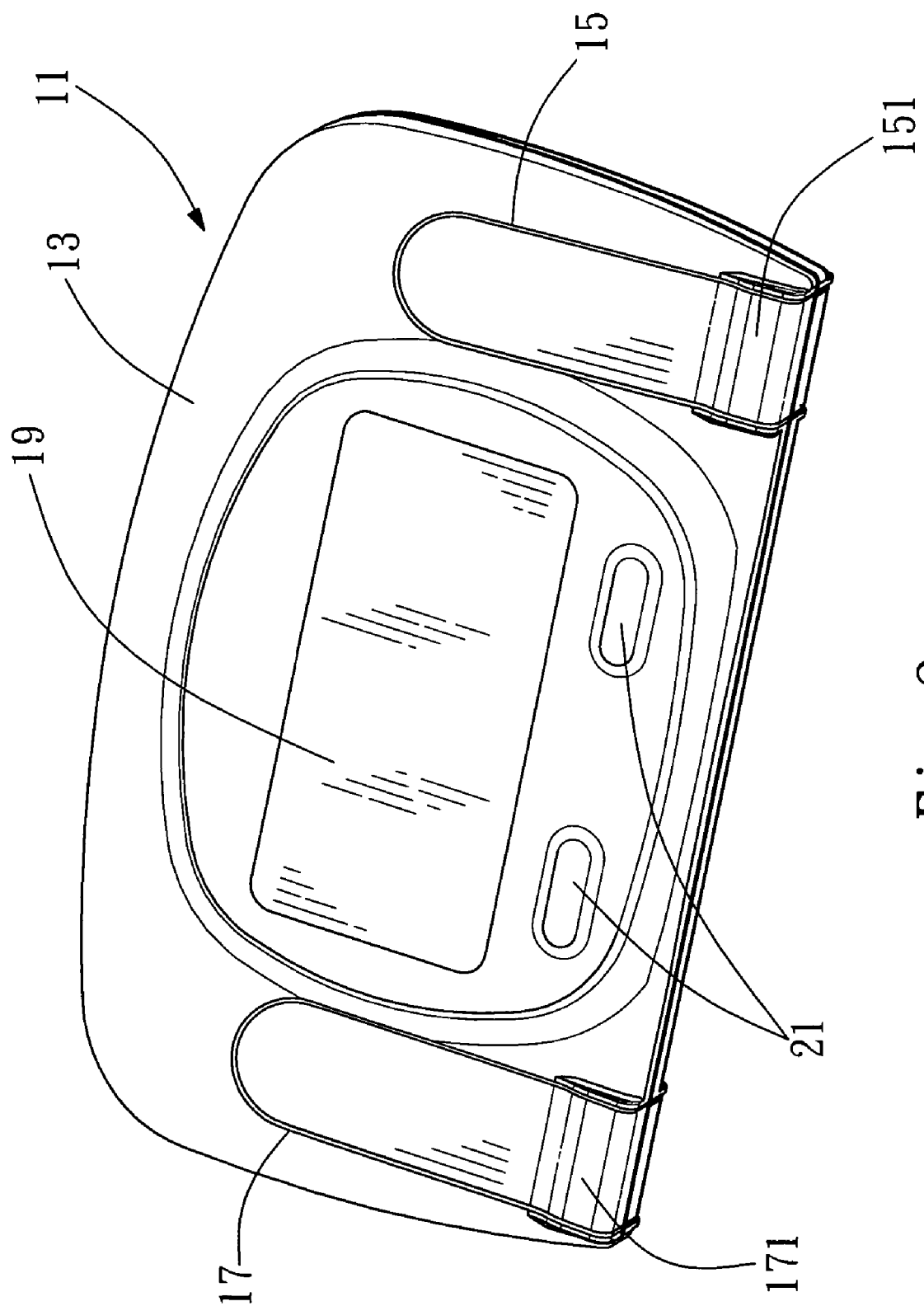
FIG. 2 is a front perspective view of a preferred embodiment of the present invent.
Figure 3:
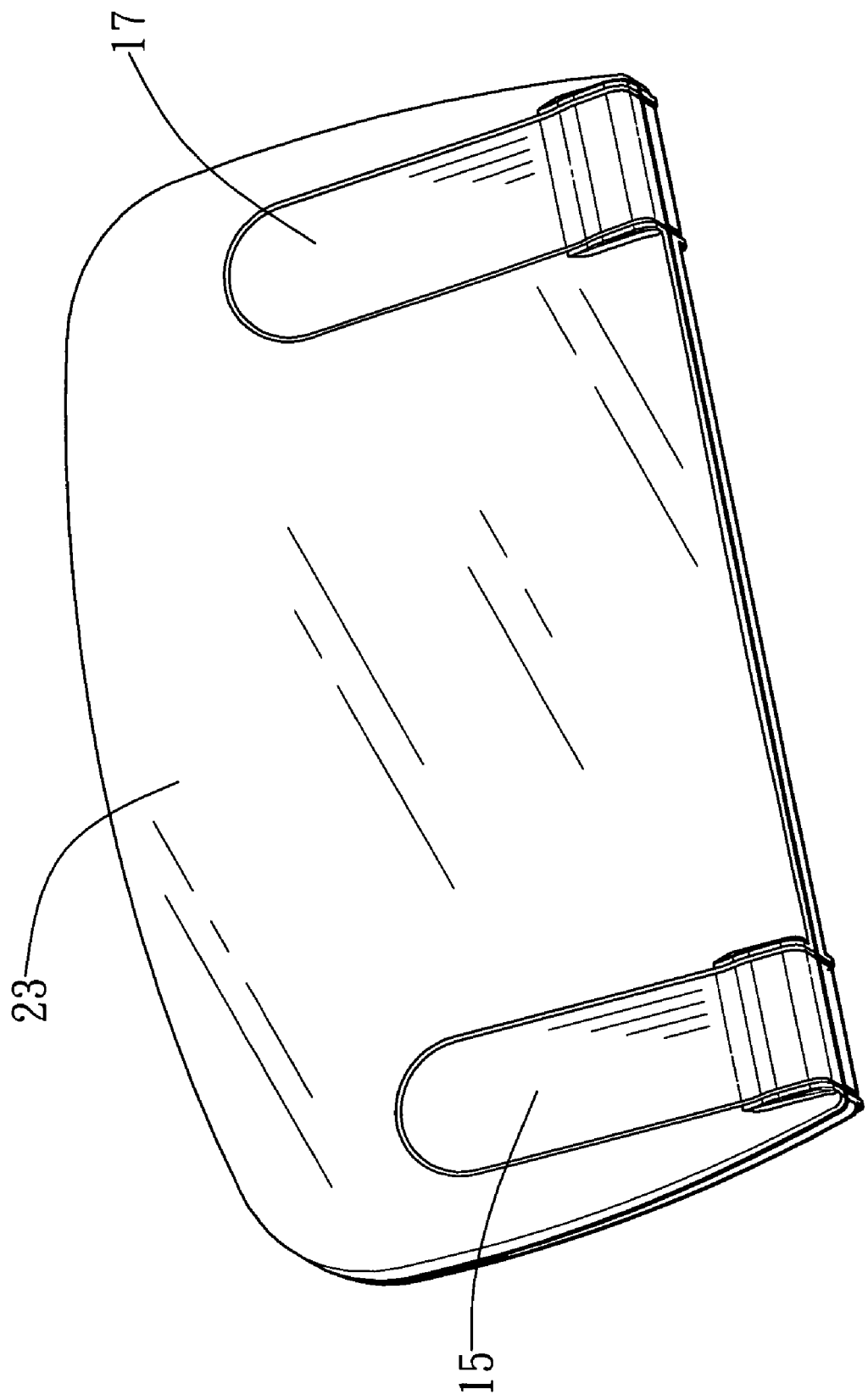
FIG. 3 is a rear perspective view of the preferred embodiment of the present invent.

Please refer to FIG. 2 and FIG. 3, which are a front perspective view and a rear perspective view of the preferred embodiment of the present invent. The present invention comprises a shell 11, shaped as a thin and long cube and has an operating panel 13. The operating panel 13 includes two buttons 21 for setting and transferring functions, gelless electrodes with a thin foil shape are provided as right and left electrodes 15, 17, and are slightly embedded and fixed in the operating panel 13, passing over an edge of the shell 11 to extend along a bottom surface 23 of the shell 11, opposite to the operating panel 13. Electrodes 15 and 17 are made of any conductive metal or conductive rubber. Further, both of electrodes 15 and 17 in the area where the electrodes pass over the edge of the shell 11, each electrode having protruding surfaces or ridges 151 and 171 to act as gripping surfaces for the root area between two fingers of each of a user's two hands to clampingly engage the respective electrodes. An information display 19, located on the operating panel 13, is provided to display a plurality of measured values. A calculation system 27 located in the shell 11 (not shown on FIG. 2 and FIG. 3) connects to the electrodes 15 and 17 and the information display 19 in order to calculate electrical information measured from the received signals of the electrodes 15 and 17, and displays the measured values on the information display 19.

Figure 4:
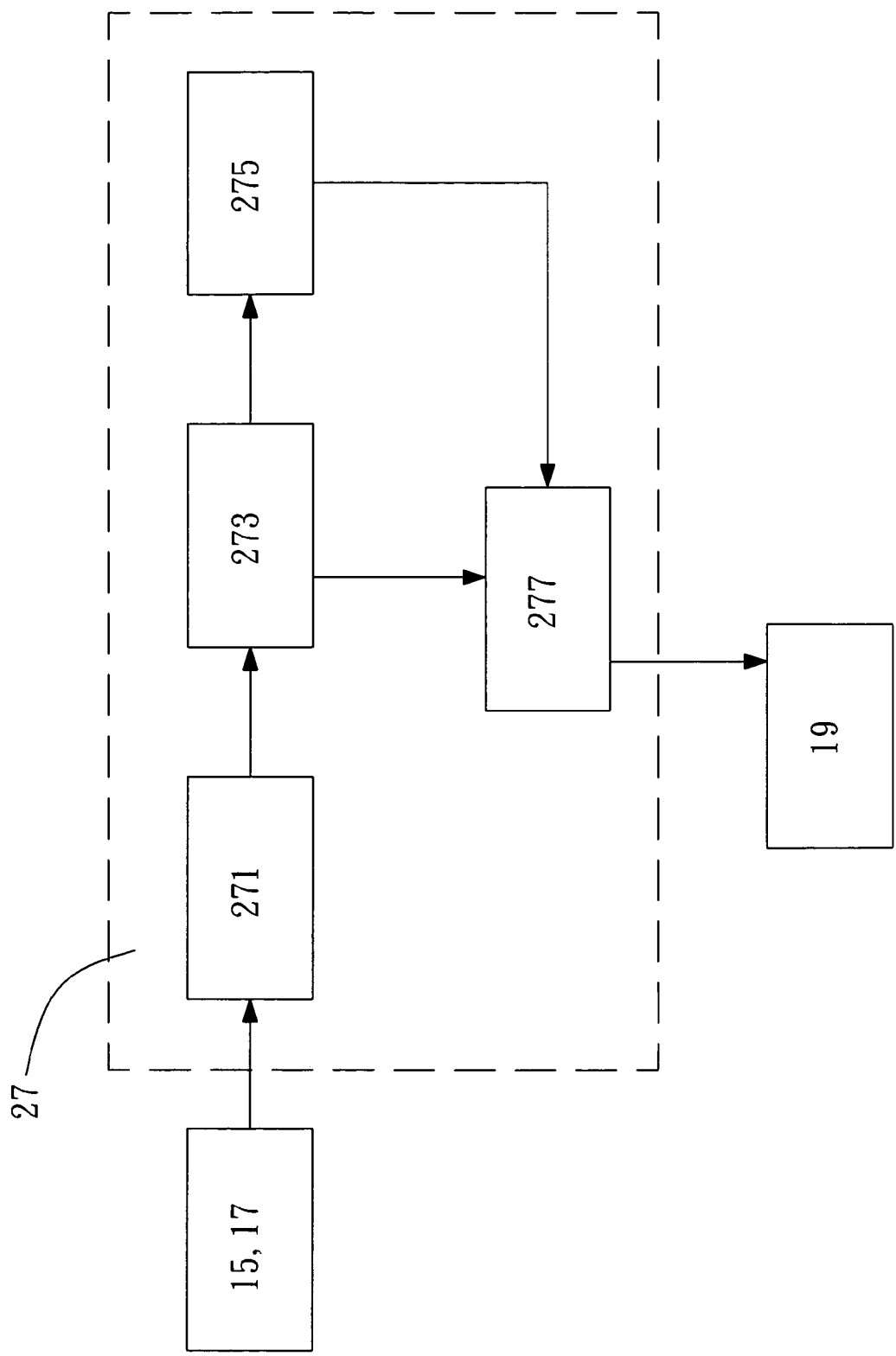
FIG. 4 is a block diagram of hardware of the calculation system of the present invention.

Please refer to FIG. 4, which is a block diagram of hardware of the calculation system of the present invention. FIG.

4 discloses a relationship among all main components in the calculation system 27, as well as the relationship among the calculation system 27, electrodes 15 and 17 and information display 19. The calculation system 27 comprises a pre-signal amplify circuit 271, an electrocardio signal amplify/filter circuit 273, an analog/digital converting circuit 275 and a CPU 277. Arrows shown in FIG. 4 represent the process flow for calculation. It means the pre-signal amplify circuit 271 amplifies signals of received electrical information and the electrocardio signal amplify/filter circuit 273, the analog/digital converter circuit 275 and the CPU 277 constantly execute calculations when the right and left electrodes 15, 17 receive electrical information. Wherein, a loop is formed by electrocardio signal amplify/filter circuit 273, analog/digital converter circuit 275 and CPU 277, whose main function is to process different information values including the ST segment, QRS interval and heartbeat rate. At last, values corresponding to that information are shown on the display 19.

Figure 5:
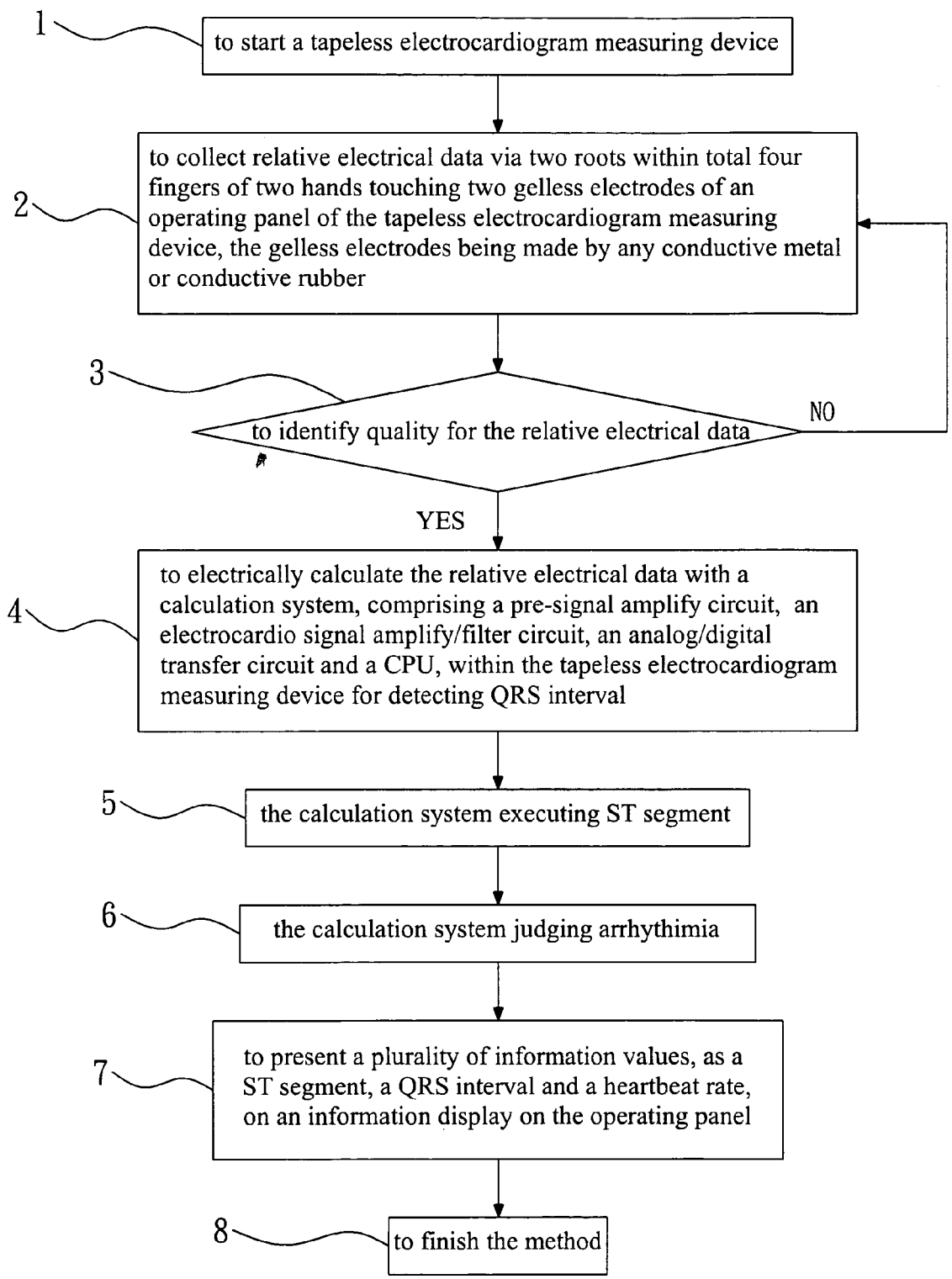
FIG. 5 is a flowchart of measuring steps of the present invention.

Please refer to FIG. 5, which is a flowchart of measuring steps of the present invention. The steps include:
  (1) starting a tapeless electrocardiogram measuring device;
  (2) collecting electrical data via root areas of two hands, wherein a total of two fingers of each of two hands respectively touch two gelless electrodes of an operating panel of the tapeless electrocardiogram measuring device, the gelless electrodes being made of any conductive metal or conductive rubber;
  (3) identifying whether the quality of the electrical data is acceptable, if unacceptable, then returning to step (2), otherwise going to next step;
  (4) calculating the relevant electrical data with a calculation system, the calculation system comprising a pre-signal amplify circuit, an electrocardio signal amplify/filter circuit, an analog/digital converter circuit and a CPU, located within the tapeless electrocardiogram measuring device for detecting the QRS interval;
  (5) the calculation system executes an ST segment;
  (6) the calculation system judges whether an arrhythmia has occurred;
  (7) presenting a plurality of information values, as an ST segment, a QRS interval and a heartbeat rate, on an information display disposed on the operating panel; and
  (8) finishing the method.

Figure 6:
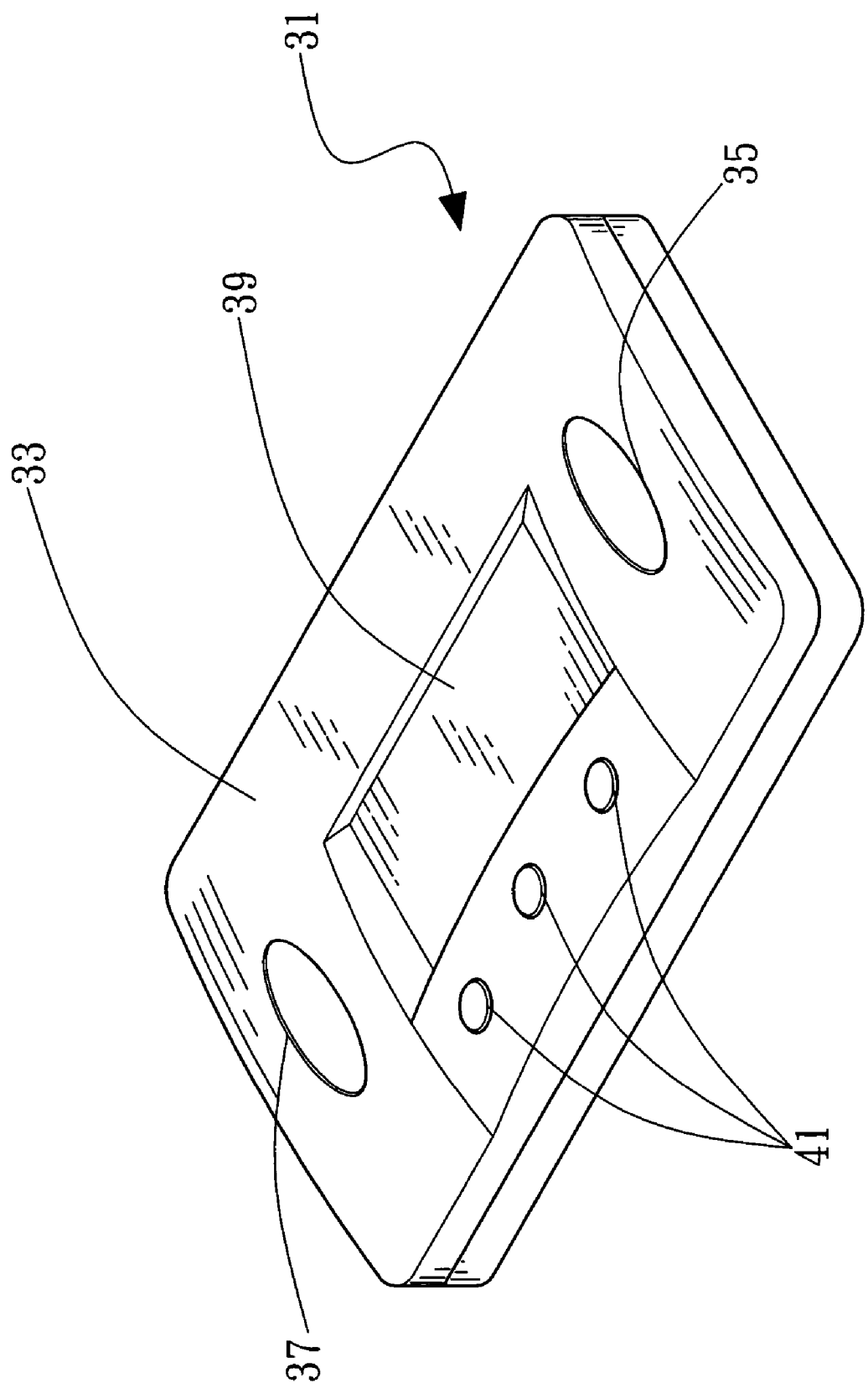
FIG. 6 is a front perspective view of a second preferred embodiment of the present invent.
Figure 7:
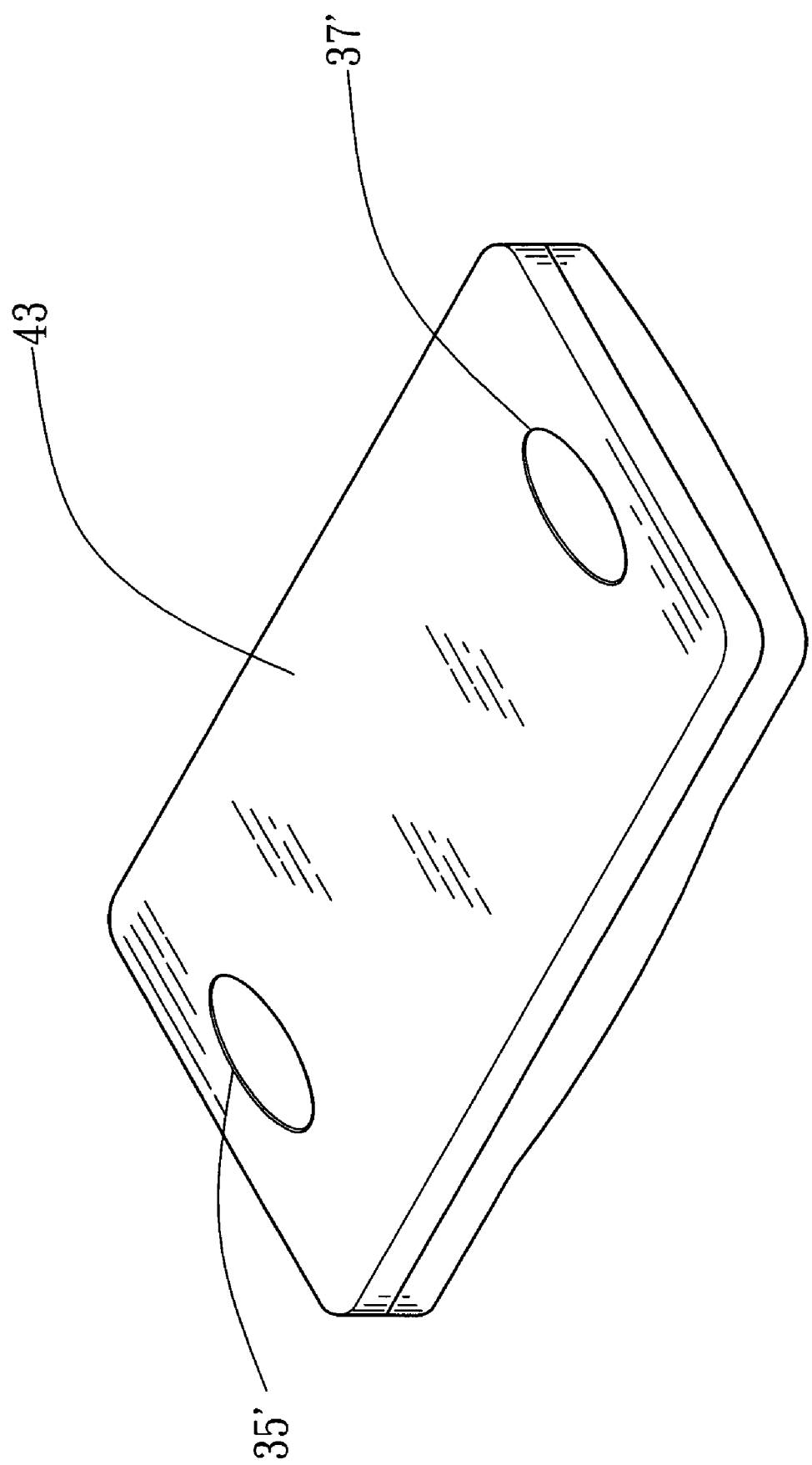
FIG. 7 is a rear perspective view of the second preferred embodiment of the present invent.

Please refer to FIG. 6 and FIG. 7, which are a front perspective view of a second preferred embodiment of the present invent and a rear perspective view of the second preferred embodiment of the present invent. The device for measuring an electrocardiogram with a tapeless format comprises a shell 31, shaped as a thin and long cube and having one operating panel 33. The operating panel 33 including three buttons 41 to set and transfer functions. The device includes four gelless electrodes, two right electrodes 35, 35' and two left electrodes 37, 37' slightly embedded and fixed in the operating panel 33 and a bottom surface 43. The gelless electrodes are made of any conductive metal or conductive rubber. One information display 39, located on the operating panel 33, is provided to display a plurality of measured values. The plurality of information values shown on the information display 39 include values of the ST segment, QRS interval and heart-beat rate. A calculation system (not shown in FIG. 6 and FIG. 7, but shown in FIG. 4), connects with the four gelless electrodes 35, 35', 37 and 37' and the information display 39, located in the shell 31, in order to calculate electrical information measured from the received signals of the gelless electrodes 35, 35', 37 and 37' and displays results on the information display 39. The calculation system includes a pre-signal amplify circuit, an electrocardio signal amplify/filter circuit, an analog/digital transfer circuit and a CPU. The pre-signal amplify circuit is connected to the gelless electrodes to receive electrical data, and results are continuously displayed on the information display 39, after calculating the electrical data by means of the electrocardio signal amplify/filter circuit and the analog/digital transfer circuit and the CPU.

Figure 8:
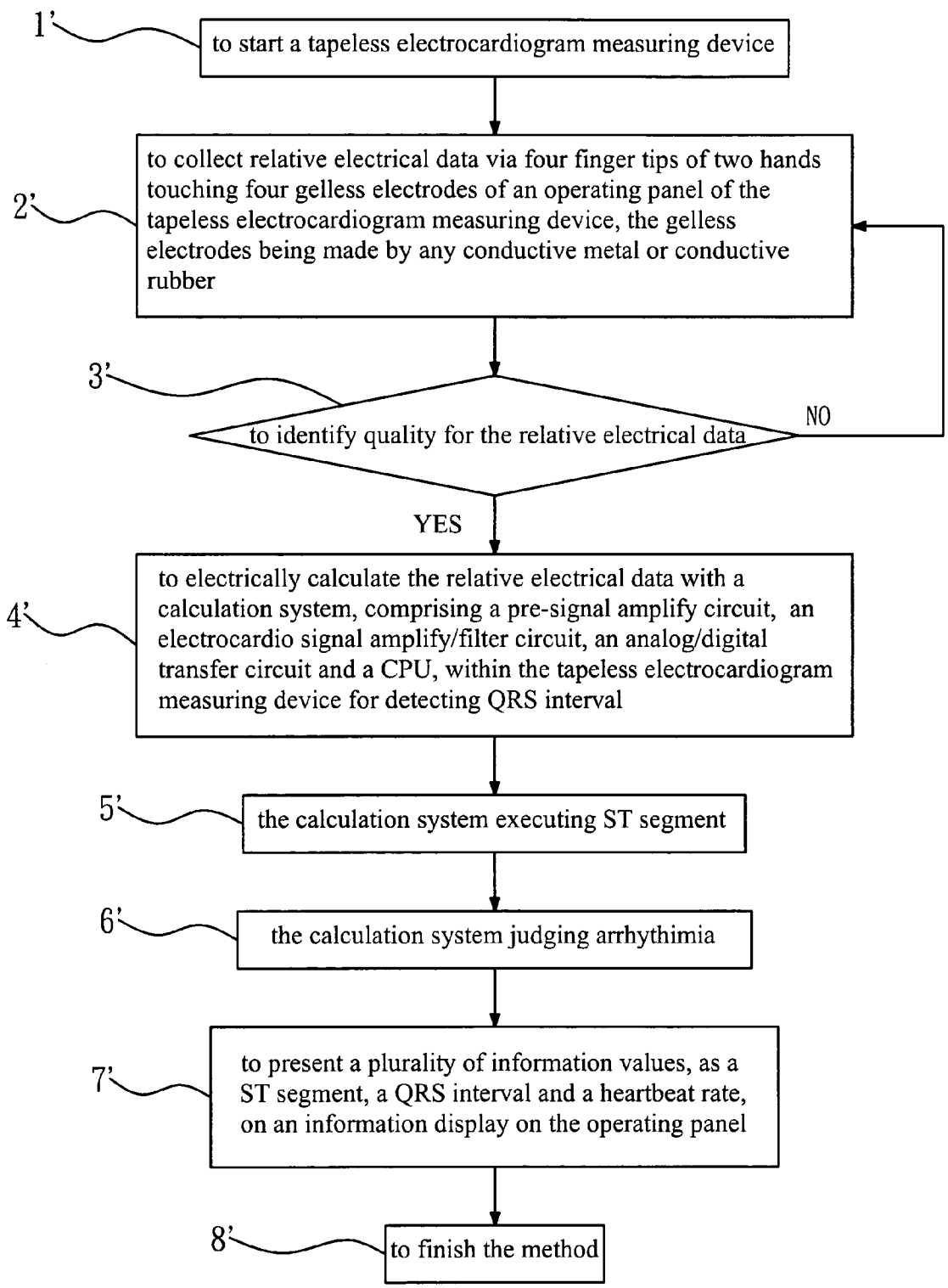
FIG. 8 is a flowchart of measuring steps of the second preferred embodiment of the present invention.

Please refer to FIG. 8, which is a flowchart of measuring steps of the second preferred embodiment of the present invention. The steps include:
  (1') starting a tapeless electrocardiogram measuring device;
  (2') collecting electrical data via two finger tips of each of two hands respectively touching four gelless electrodes of an operating panel of the tapeless electrocardiogram measuring device, the gelless electrodes being made of any conductive metal or conductive rubber;
  (3') identifying whether the quality of the electrical data is acceptable, if unacceptable, then returning to step (2), otherwise going to next step;
  (4') calculating the relevant electrical data with a calculation system, the calculation system comprising a pre-signal amplify circuit, an electrocardio signal amplify/filter circuit, an analog/digital converter circuit and a CPU, located within the tapeless electrocardiogram measuring device for detecting the QRS interval;
  (5') the calculation system executes an ST segment;
  (6') the calculation system judges whether an arrhythmia has occurred;
  (7') presenting a plurality of information values, as an ST segment, a QRS interval and a heartbeat rate, on an information display disposed on the operating panel; and
  (8') finishing the method.

Figure 9:
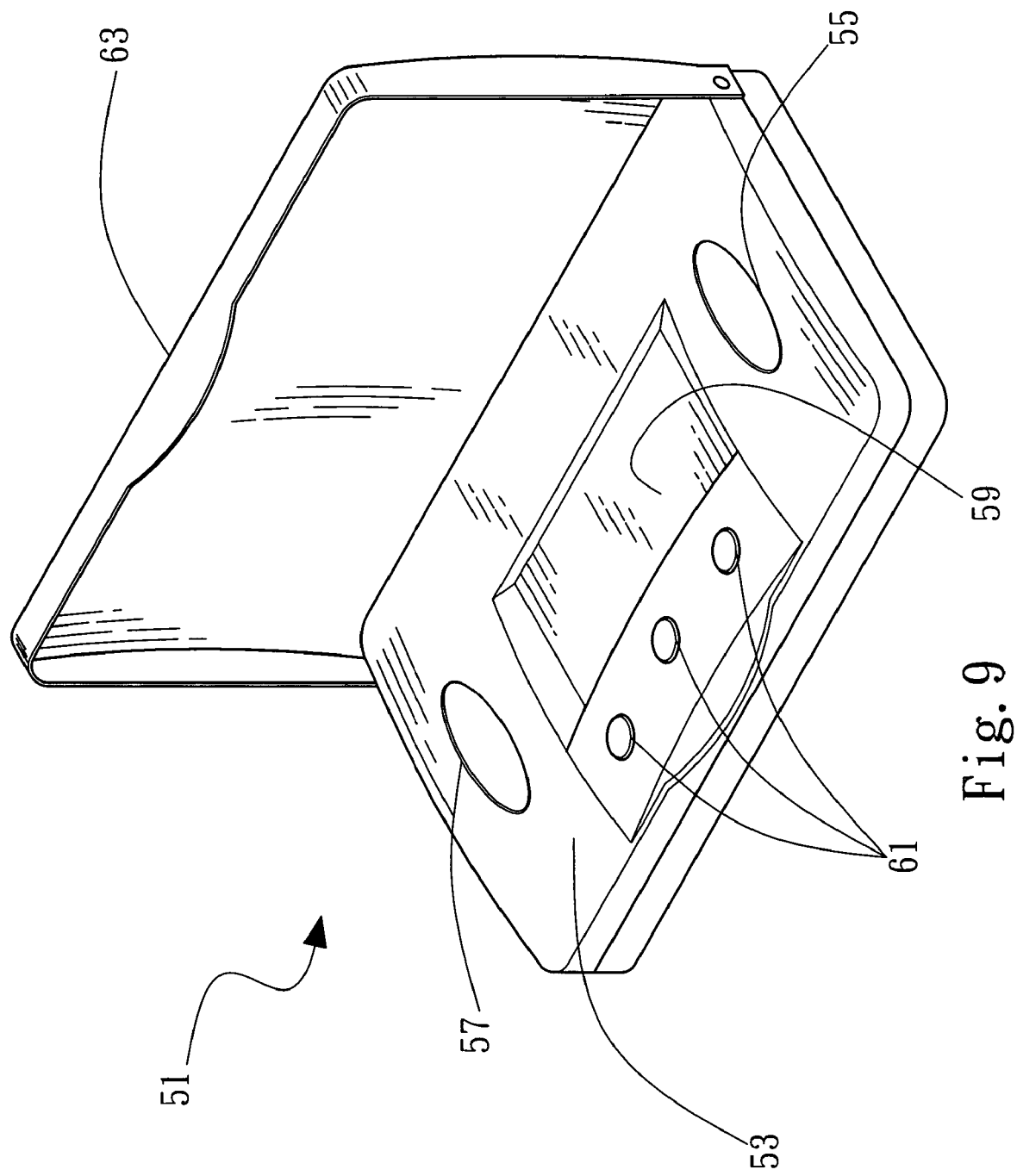
FIG. 9 is a front perspective view of a third preferred embodiment of the present invent.

Please refer to FIG. 9, which is a front perspective view of a third preferred embodiment of the present invent. The device for measuring an electrocardiogram with a tapeless format comprises a cover 63, and a shell 51, shaped as a thin and long cube and having one operating panel 53. The operating panel 53 includes three buttons 61 to set and transfer functions and two gelless electrodes 55 and 57, slightly embedded and fixed in the operating panel 53. The gelless electrodes are made of any conductive metal or conductive rubber. The device includes one information display 59, located on the operating panel 53, to display a plurality of measured values. The plurality of information values shown on the information display 59 include values of the ST segment, QRS interval and heart-beat rate. A calculation system located in the shell 51 (not shown in FIG. 9, but shown in FIG. 4), connects with the two gelless electrodes 55 and 57 and the information display 59 in order to calculate electrical information measured from the received signals of the gelless electrodes 55 and 57 and displays results on the information display 59. The calculation system further comprising a pre-signal amplify circuit, an electrocardio signal amplify/filter circuit, an analog/digital transfer circuit and a CPU, wherein the pre-signal amplify circuit connected to the gelless electrodes to get electrical data, and results are continuously displayed on the information display 59 after calculating the electrical data by means of the electrocardio signal amplify/filter circuit and the analog/digital converter circuit and the CPU.

Figure 10:
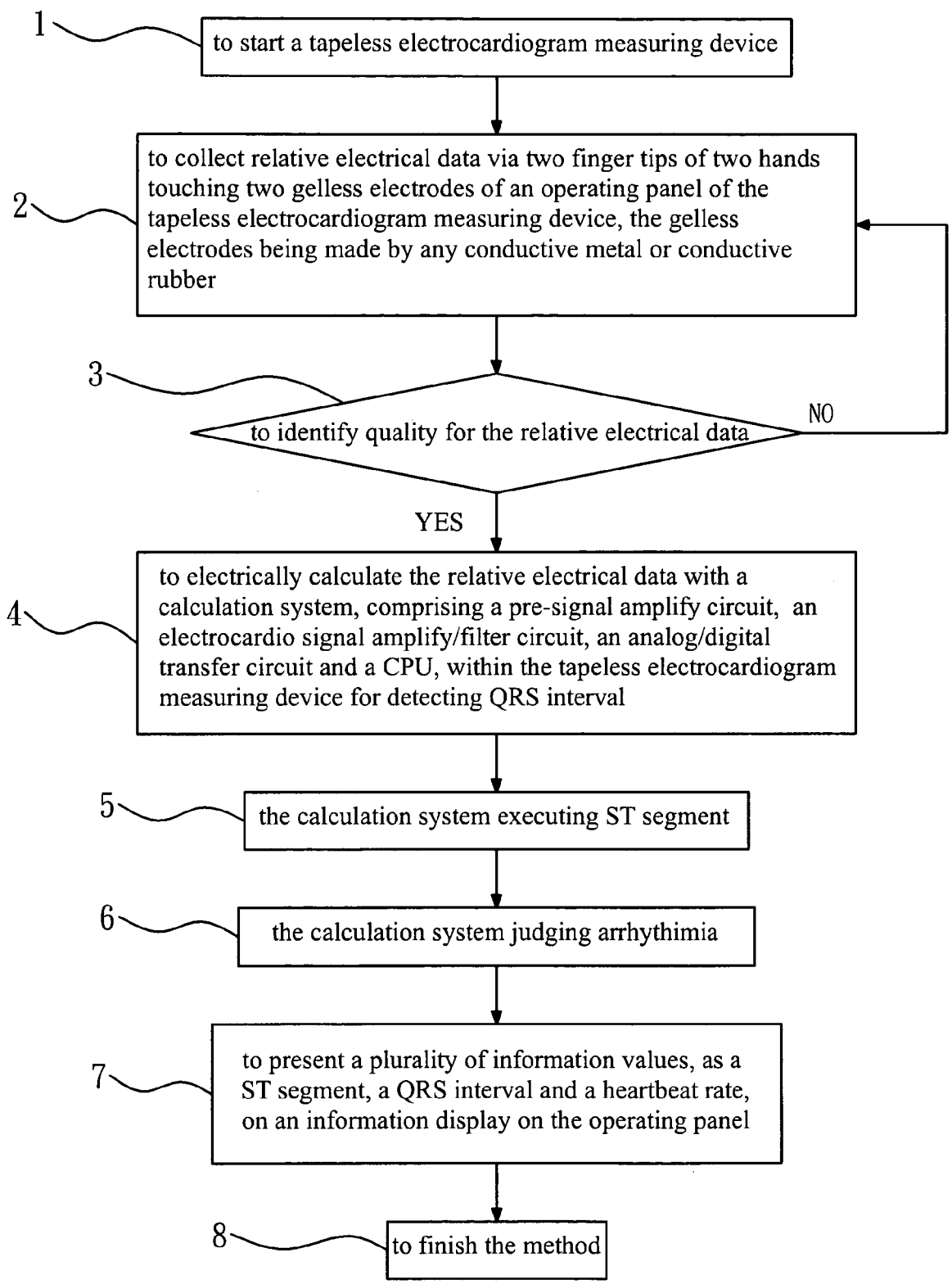
FIG. 10 is a flowchart of measuring steps of the third preferred embodiment of the present invention.

Please refer to FIG. 10, which is a flowchart of measuring steps of the third preferred embodiment of the present invention. The steps include:
  (1") starting a tapeless electrocardiogram measuring device;
  (2") collecting electrical data via a finger tip of each of two hands respectively touching two gelless electrodes of an operating panel of the tapeless electrocardiogram measuring device, the gelless electrodes being made of any conductive metal or conductive rubber;

(3") identifying whether the quality of the electrical data is acceptable, if unacceptable, then returning to step (2), otherwise going to next step;

(4") calculating the relevant electrical data with a calculation system, the calculation system comprising a pre-signal amplify circuit, an electrocardio signal amplify/filter circuit, an analog/digital converter circuit and a CPU, located within the tapeless electrocardiogram measuring device for detecting the QRS interval;

(5") the calculation system executes an ST segment;

(6") the calculation system judges whether an arrhythmia has occurred;

(7") presenting a plurality of information values, as an ST segment, a QRS interval and a heartbeat rate, on an information display disposed on the operating panel; and (8") finishing the method.

The device for measuring an electrocardiogram with a tapeless format, as described above, can be incorporated with other electrical products, which can be one of the following: a mobile phone, a walkie-talkie, a portable computer, and a walkman.

Known from the above description, the present invention adopts a unique measuring method that is completely different the prior, to collect the physiological electrical data by touching two thin electrodes with the root portion between two fingers of each of a user's two hands or electrodes embedded thereon being touched with two fingers of each of the user's two hands. Wherein, there are only two thin electrodes used without smearing any conductive material on the user's skin or the electrodes, and the present invention can be used instead of the complex measuring process with pasting electrodes on the hands, the ankles and the chest. On the other hand, the measuring apparatus of the present invention can be sterilized and is lighter due to its easier measuring method.

It is to be understood that while the invention has been described above in conjunction with preferred specific embodiments, the description and examples are intended to illustrate and not limit the scope of the invention, which is defined by the scope of the appended claims.

What is claimed is:

1. A device for measuring electrocardiogram with tapeless format comprising:
   a shell being shaped as a thin and long cube and having
      a top surface having
         a left side;
         a right side;
         a right upper finger touching area located on the right side of the top surface;
         a left upper finger touching area located on the left side of the top surface and being parallel with the right upper finger touching area;
      a bottom surface being opposite to the top surface having;
         a left side;
         a right side;
         a right lower finger touching area located on the right side of the bottom surface; and
         a left lower finger touching area located on the left side of the bottom surface and being parallel with the right lower finger touching area;
      a front edge vertically formed between the top and bottom surfaces;
      a right edge vertically formed between the top and bottom surfaces;
      a left edge vertically formed between the top and bottom surfaces; and
      a rear edge vertically formed between the top and bottom surfaces;
   a right finger gelless electrode with a thin foil shape having
      a right upper gelless electrode portion embedded in the right upper finger touching area of the top surface and being distant from the right, left and rear edges;
      a right lower gelless electrode portion formed on the right lower finger touching area of the lower surface and being distant from the right, left and rear edges; and
      a right middle gelless electrode portion formed on the front edge and connected between the right upper and lower gelless electrodes and being distant from the right and left edges;
   a left finger gelless electrode with a thin foil shape having
      a left upper electrode portion embedded in the left upper finger touching area of the top surface and being distant from the right, left and rear edges;
      a left lower electrode portion formed on the left lower finger touching area of the lower surface and being distant from the right, left and rear edges; and
      a left middle electrode portion formed on the front edge and connected between the left upper and lower electrodes and being distant from the right and left edges;
   at least one information display located on the top surface to display a plurality of measured values; and
   a calculation system mounted in the shell and connected to the two gelless electrodes and the information display for calculating relative electrical information measured from the gelless electrodes and display results on the information display.

2. The device for measuring an electrocardiogram with tapeless format as recited in claim 1, wherein the operating panel has at least one button to set and transfer functions.

3. The device for measuring an electrocardiogram with tapeless format as recited in claim 1, wherein each of the gelless electrodes is made of any conductive metal or rubber.

4. The device for measuring an electrocardiogram with tapeless format as recited in claim 1, wherein information values shown on the information display include at least values of ST segment, QRS interval and heart-beat rate.

5. The device for measuring an electrocardiogram with tapeless format as recited in claim 1, wherein the calculation system further comprises:
   a pre-signal amplify circuit;
   an electrocardio signal amplify/filter circuit;
   an analog/digital transfer circuit; and
   a CPU;
   wherein the pre-signal amplify circuit is connected to the gelless electrodes to receive relative electrical data, and the calculation system continuously displays results on the information display after calculating the electrical data by means of the electrocardio signal amplify/filter circuit and the analog/digital transfer circuit and the CPU.

* * * * *